United States Patent [19]

Repman et al.

[11] Patent Number: 5,107,040

[45] Date of Patent: Apr. 21, 1992

[54] DEHYDROHALOGENATION USING MAGNESIUM HYDROXIDE

[75] Inventors: Joseph F. Repman; Tarver G. Snedecor, Jr., both of Angleton, Tex.

[73] Assignee: The Dow Chemical Company, Midland, Mich.

[21] Appl. No.: 701,400

[22] Filed: May 15, 1991

[51] Int. Cl.$^5$ .............................................. C07C 17/34
[52] U.S. Cl. ........................................................ 570/228
[58] Field of Search ........................................... 570/228

[56] References Cited

U.S. PATENT DOCUMENTS

| | | | |
|---|---|---|---|
| 2,134,102 | 10/1938 | Cass | 260/654 |
| 2,410,541 | 11/1946 | Joyce | 260/654 |
| 2,598,646 | 5/1952 | Maude et al. | 260/654 |
| 3,290,398 | 12/1966 | Richtzenhain et al. | 260/654 |
| 3,622,641 | 11/1971 | Crary | 260/655 |
| 3,639,492 | 2/1972 | Campbell | 260/655 |
| 3,639,493 | 2/1972 | Campbell | 260/655 |
| 3,725,486 | 3/1973 | McCracken et al. | 570/229 |
| 3,754,044 | 8/1973 | Hargraves et al. | 260/654 |
| 3,869,520 | 3/1975 | Gordon | 260/654 |

Primary Examiner—Howard T. Mars
Assistant Examiner—Kimberly J. Kestler

[57] ABSTRACT

A process comprising contacting a solvent, magnesium hydroxide, and a halogenated hydrocarbon at a pressure sufficient to keep the solvent and the halogenated hydrocarbon under liquid conditions, and a temperature greater than 150° C. under conditions suitable to dehydrohalogenate the halogenated hydrocarbon, and recovering the dehydrohalogenated product.

9 Claims, No Drawings

DEHYDROHALOGENATION USING MAGNESIUM HYDROXIDE

BACKGROUND OF THE INVENTION

The present invention relates to a method for dehydrohalogenating a halogenated hydrocarbon by contacting the compound with a solution containing magnesium hydroxide at high temperatures and pressures.

Polychlorinated ethanes can all be dehydrochlorinated to corresponding chloroethylenes which are used commercially. For example, 1,2-dichlorethane yields vinyl chloride, the well-known monomer for the production of polyvinylchloride; the tetrachloroethanes yield trichloroethylene, a widely used industrial degreasing solvent; and pentachloroethane yields perchloroethylene, the widely used nonflammable drycleaning solvent. Depending on the dehydrohalogenation method, 1,1,2-trichlorethane may yield all three isomeric dichloroethylenes or predominantly only one of the dichloroethylenes. Of the three isomers only 1,1-dichloroethene (vinylidene chloride) has found wide use. In addition to its use as a monomer for polymer production, it has also become an intermediate for the production of herbicides, latexes, and 1,1,1-trichloroethane which is used as a degreasing solvent. Therefore, the method which yields predominantly vinylidene chloride is preferred.

The classical method of dehydrochlorinating the polychloroethanes employs an aqueous suspension of alkaline earth hydroxides such as calcium or barium hydroxide. In general, these reactions are run under ambient pressures at a temperature at or below the boiling point of the chlorinated reactant. For example, U.S. Pat. No. 2,598,646 discloses a continuous process for dehydrochlorinating a polychloroethane by contacting an aqueous alkaline earth metal hydroxide slurry in a closed chamber with a polychloroethane at a reaction temperature below the boiling point of any of the organic azeotropes formed therein. While the examples report good yield using calcium hydroxide, data for magnesium hydroxide is not provided. It is known, however, that the process produces poor conversions to vinylidene chloride when magnesium hydroxide is used as the alkaline earth metal hydroxide in such a process.

More recently, methods employing an aqueous solution of an alkali metal hydroxide dispersed in the organic chloroethane phase by means of powerful mixing devices have found widespread use. These reactions are typically run at or below the boiling point of the chlorinated reactant and under ambient pressures. In these cases, extreme care must be taken to avoid an excess of the hydroxide. Otherwise, the vinylidene chloride product can undergo dehydrochlorination to hazardous acetylenic compounds. Due to the potential of producing acetylenic compounds, less than stoichiometric amounts of alkali metal hydroxides are typically used.

Therefore, the existing problem is that the use of magnesium hydroxide by itself has been unsuccessful due to the poor solubility of the hydroxide ion. Due to the widespread availability, low cost, and other advantages described herein, it would be advantageous to the chemical industry and to the public to possess a method whereby magnesium hydroxide could be used to dehydrohalogenate halogenated organic compounds. Such a process would provide another route to vinylidene chloride when, for example, the price of caustic is high. It would also be advantageous to have a method whereby the product can be selectively formed without precise equivalent mixtures of reactant and base, and wherein the formation of potentially explosive acetylene compounds does not occur.

SUMMARY OF THE INVENTION

It has now been found that magnesium hydroxide can be used successfully in a dehydrohalogenation process by contacting dehydrohalogenatable halogenated hydrocarbon, a solvent, and magnesium hydroxide at temperatures above about 150° C. and pressures sufficient to keep both the hydrocarbon and solvent under liquid conditions.

The process of the present invention makes it possible to use magnesium hydroxide as the sole base to dehydrohalogenate halogenated hydrocarbons. Excess magnesium hydroxide does not produce acetylenes and, therefore, a stoichiometric amount of magnesium hydroxide is not required in the process of the present invention. Thus, the method of the present invention is simple and safe to use. The public, moreover, is benefited by a new dehydrohalogenation method using an inexpensive alternative to caustic which is commonly employed in dehydrohalogenation processes today.

DETAILED DESCRIPTION OF THE INVENTION

The dehydrohalogenation process of the present invention is generally employed to dehydrohalogenate halogenated hydrocarbon using a solution containing magnesium hydroxide.

The temperature at which the method of the present invention will operate is preferably above about 150° C. More preferably, the temperature is between about 150° C. and 300° C., and most preferably between about 175° C. and 225° C.

The pressure at which the present invention will operate is any pressure effective to keep both the halogenated hydrocarbon and solvent in the liquid phase. Sufficient pressure may thus be any pressure at or above the combined vapor pressure of the solvent and reactants at a given temperature. Preferably, the pressure is above about 175 psig. As used herein "psig" is defined as pounds per square inch gauge. More preferably, the pressure is between about 175 and 500 psig, most preferably between about 250 and 400 psig.

The apparatus which are useful in the present invention are known in the art and are any which will enable the invention to be carried out at elevated pressures and temperatures so as to dehydrohalogenate halogenated alkanes using a solution containing magnesium hydroxide. For example, a plug flow or stirred tank reactor may be used. Likewise, a useful apparatus can be employed which runs batch, semicontinuous, or continuous reactions; preferably a continuous reaction is run. Preferably, the apparatus allows the dehydrohalogenated products of the present invention to be continuously removed from the reaction zone. Methods of recovering the products formed by the method of the present invention are well known to those skilled in the art. For example, distillation is often employed to separate and further purify the product.

The process of the present invention is carried out in the liquid phase. In a preferred embodiment, the solution containing the magnesium hydroxide is contacted with the halogenated hydrocarbon under vigorous agitation.

The solvent used to dissolve magnesium hydroxide is typically water. Other solvents may, however, be used as co-solvents if the halogenated hydrocarbon has low solubility in water during the process of the present invention. Examples of such cosolvents include glycols and alcohols such as methanol, ethanol, the propyl alcohols, and the like. Thus, multi-component solvents may be used in the present invention such as mixed water-alcohol or glycol-water solvent systems. The most preferred solvent is water.

In its broadest application, the present invention is useful to allow bases which do not have appreciable solubility in water at temperatures up to about 150° C. and under ambient pressures to enter solution in amounts sufficient to dehydrohalogenate halogenated hydrocarbons. Most preferably, magnesium hydroxide is the base.

The concentration of base in the solvent may be in the range between about 0.1 and 75 percent by weight. Preferably, the concentration of base in the solvent is between about 10 and 50 percent by weight, more preferably, between about 15 and 35 percent by weight. Importantly, the molar ratio of base to halogenated hydrocarbon can be less than, equal to, or more than the stoichiometric amount. Preferably, the molar ratio of base to halogenated hydrocarbon is between about 1:1 and 10:1, more preferably between about 2:1 and 5:1.

The halogenated hydrocarbons which are useful in the present invention include halogenated alkanes having one or more halogen atoms and having two or more carbon atoms. The halogenated hydrocarbons useful in the present invention must be capable of being dehydrohalogenated. Compounds containing more than one halogen may have two or more types of halogen atoms. The preferred halogens are bromine, iodine, and chlorine. The halogenated hydrocarbons may be haloalkanes, aliphatic compounds containing a halo-alkyl group, or aromatic compounds containing a halo-alkyl group. Preferably, the hydrocarbon is a straight-chain, branched, or cyclic organic compound having from 2 to 6 carbon atoms and the halogen atom is chlorine. Most preferred halogenated hydrocarbons include 1,1,2-trichloroethane; 1,1-dichloroethane; 1,1,1-trichloroethane; 1,2-dichloroethane; chloroethane, 1,1,1,2-tetrachloroethane, 1,1,2,2-tetrachloroethane, pentachloroethane, pentachloroethane or mixtures thereof.

SPECIFIC EMBODIMENTS OF THE INVENTION

The following examples are given to illustrate the invention and should not be construed as limiting its scope. All parts and percentages are by weight unless otherwise indicated.

EXAMPLE 1

Batch Synthesis of Vinylidene Chloride

In a batch reaction apparatus, 27.3 grams of 1,1,2-trichloroethane is added to 202.7 grams of a 7.8 weight percent aqueous magnesium hydroxide solution. With continuous stirring, the mixture is heated to maintain a temperature in the range between about 190° to 200° C. and is pressurized to maintain about a 200 psig nitrogen atmosphere. After 45 minutes from time of addition, the product is collected and analyzed. The analysis data shows 86.5% conversion of the 1,1,2,-trichloroethane and 98.6% selectivity to vinylidene chloride.

EXAMPLE 2

Continuous Synthesis of Vinylidene Chloride

In an apparatus designed to run continuous high pressure and temperature reactions, the following data is generated in Table I for reactions using water as the solvent, magnesium hydroxide as the base, and 1,1,2-trichloroethane as the halogenated hydrocarbon. Acetylenic compounds are not detected in any run.

TABLE I

| Temperature °C. | Pressure (psig) | $Mg(OH_2)$ Concentration in Solvent (% by weight) | Molar ratio of 1,1,2-trichloroethane to $Mg(OH)_2$ | Residence Time (Minutes) | Conversion (%) | Selectivity (%) |
|---|---|---|---|---|---|---|
| 185 | 275 | 0.15 | .5 | 5.0 | 55 | 99 |
| 200 | 375 | 0.15 | 1.5 | 12.5 | 70 | 97 |
| 220 | 375 | 0.15 | 1.5 | 12.5 | 67 | 96 |
| 180 | 375 | 0.15 | 1.5 | 12.5 | 40 | 98 |
| 200 | 375 | 0.15 | 0.6 | 12.3 | 86 | 97 |
| 220 | 375 | 0.15 | 0.6 | 12.3 | 78 | 96 |
| 220 | 375 | 0.32 | 0.26 | 19.7 | 82 | 96 |
| 201 | 375 | 0.32 | 0.26 | 19.7 | 85 | 97 |
| 200 | 375 | 0.32 | 0.64 | 12.5 | 62 | 97 |
| 220 | 375 | 0.32 | 0.24 | 12.6 | 77 | 96 |
| 222 | 375 | 0.31 | 0.63 | 19.7 | 64 | 96 |
| 221 | 375 | 0.31 | 1.0 | 12.5 | 45 | 97 |
| 202 | 275 | 0.31 | 0.26 | 19.5 | 75 | 97 |
| 199 | 275 | 0.31 | 1.0 | 19.9 | 43 | 97 |
| 179 | 275 | 0.31 | 0.6 | 19.9 | 58 | 98 |
| 201 | 275 | 0.31 | 0.6 | 19.9 | 45 | 97 |
| 182 | 275 | 0.31 | 0.9 | 13.1 | 34 | 97 |
| 201 | 275 | 0.31 | 0.6 | 12.2 | 47 | 98 |
| 180 | 275 | 0.34 | 0.26 | 12.6 | 60 | 99 |
| 200 | 275 | 0.33 | 0.28 | 20.5 | 67 | 96 |
| 200 | 275 | 0.33 | 0.26 | 12.4 | 62 | 99 |

From the examples it can be seen that halogenated hydrocarbons may be converted to alkenyl compounds using magnesium hydroxide as the sole base. The reaction produces product free of acetylenic compounds despite the use of a large excess of base. The reaction produces high conversions and high selectivity toward vinylidene chloride from 1,1,2-trichloroethane. While selectivity to vinylidene chloride remains relatively constant as variables are changed, conversion increases using longer residence times, higher ratios of base to halogenated hydrocarbon, and temperatures at or above 200° C.

What is claimed is:

1. A process comprising contacting a solvent, magnesium hydroxide, and a halogenated hydrocarbon selected from the group consisting of chloroethane, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, and mixtures thereof at a pressure sufficient to keep the solvent and the halogenated hydrocarbon in the liquid phase, and a temperature greater than 150° C. under conditions suitable to dehydrohalogenate the halogenated hydrocarbon, and recovering the dehydrohalogenated product.

2. The process of claim 1 wherein the halogenated hydrocarbon is 1,1,2-trichloroethane.

3. The process of claim 1 wherein the solvent is water.

4. The process of claim 1 wherein the pressure is between about 200 psig and 500 psig.

5. The process of claim 1 wherein the pressure is between about 250 psig and 400 psig.

6. The process of claim 1 wherein the temperature is between about 150° C. and 250° C.

7. The process of claim 1 wherein the temperature is between about 175° C. and 225° C.

8. The process of claim 1 wherein the molar ratio of magnesium hydroxide to halogenated hydrocarbon is between about 1:1 and 10:1.

9. A process which comprises contacting water, 1,1,2-trichloroethane, and magnesium hydroxide at a pressure between about 250 psig and 400 psig and a temperature between about 175° C. and 225° C., the molar ratio of magnesium hydroxide to 1,1,2-trichloroethane greater than 1:1, the weight percentage of magnesium hydroxide to water between about 10 and 50, under conditions suitable to dehydrohalogenate 1,1,2-trichloroethane, and recovering the vinylidene chloride so formed.

* * * * *